United States Patent
Wiggins et al.

[11] Patent Number: 5,874,619
[45] Date of Patent: Feb. 23, 1999

[54] REDUCING THE COLORATION OF AROMATIC DIAMINES

[75] Inventors: Paul L. Wiggins; Gregory H. Lambeth; William R. Brown, all of Baton Rouge, La.

[73] Assignee: Albemarle Corporation, Richmond, Va.

[21] Appl. No.: 56,600

[22] Filed: Apr. 7, 1998

[51] Int. Cl.⁶ .................................................. C07C 209/38
[52] U.S. Cl. .............................................................. 564/437
[58] Field of Search .............................................. 564/437

[56] References Cited

U.S. PATENT DOCUMENTS

| | | | |
|---|---|---|---|
| 3,408,422 | 10/1968 | May | 260/837 |
| 3,432,578 | 3/1969 | Martin | 260/880 |
| 3,644,278 | 2/1972 | Klemchuk | 260/45.8 N |
| 3,778,464 | 12/1973 | Klemchuk | 260/482 P |
| 3,926,909 | 12/1975 | Wei | 260/45.85 A |
| 4,316,996 | 2/1982 | Collonge et al. | 568/784 |
| 4,386,224 | 5/1983 | Deetman | 568/703 |
| 4,717,748 | 1/1988 | Revichandran et al. | 524/236 |

FOREIGN PATENT DOCUMENTS 59-42346  3/1984  Japan.

*Primary Examiner*—Brian M. Burn
*Attorney, Agent, or Firm*—E. E. Spielman, Jr.

[57] ABSTRACT

Existing coloration of a liquid ring-polyalkyl-substituted aromatic primary diamine is reduced by blending into such diamine a color-reducing amount of at least one dihydrocarbylhydroxylamine. Preferably, the resultant product is stored in a closed container under an inert atmosphere.

19 Claims, No Drawings

REDUCING THE COLORATION OF AROMATIC DIAMINES

BACKGROUND

Certain highly ring-substituted liquid aromatic diamines such as diethyltoluenediamine are effective curatives (curing agents) for polyurethanes and epoxy resins. Other uses include use as extenders for polyurethane elastomers, particularly in RIM applications, use as monomers, and use as antioxidants for elastomers, lubricants, and industrial oils. Unfortunately such highly substituted liquid aromatic diamines are highly sensitive to development of coloration, so much so that even when such materials are produced under an inert atmosphere such as nitrogen, color can develop when transferring the diamine product into containers. Prevention of such color development in commercial plant facilities cannot be accomplished economically.

During storage after exposure to air the coloration of such highly ring-substituted liquid aromatic diamines typically becomes progressively darker, even to the point at which the material appears almost like black ink to the naked eye. To ameliorate this problem it has been recommended that the purchaser of such a product maintain the product under a nitrogen atmosphere during storage to at least keep the existing yellow or amber coloration from reaching the black stage.

Since coloration in the product can detract from its sales appeal, a need has existed for an effective, economical way of decolorizing such aromatic diamine.

In Japan Kokai No. SHO 59-42346 published on Mar. 8, 1984 it is shown that m-phenylenediamine which initially had a standard color rating of 200 remained at the same color level for 3 days after addition thereto of 0.5% of diethylhydroxylamine, and thereafter suffered an increase in coloration to a rating of 300 at 7 days after the addition.

THE INVENTION

Contrary to the results reported in Japan Kokai No. SHO 59-42346, it has been found pursuant to this invention that incorporation of a suitable concentration of an N,N-dihydrocarbylhydroxylamine such as N,N-diethylhydroxylamine in a liquid ring-polyalkyl-substituted aromatic diamine such as diethyltoluenediamine in which coloration has already developed can promptly reduce the coloration of the diamine. Moreover by maintaining the so-treated ring-polyalkyl-substituted aromatic diamine under an inert atmosphere such as nitrogen the reduced coloration can be maintained for substantial periods of time.

Accordingly, one of the embodiments of this invention is a method of reducing the existing coloration of a liquid ring-polyalkyl-substituted aromatic diamine, which method comprises blending into said diamine a color-reducing amount of at least one N,N-dihydrocarbylhydroxylamine, most preferably N,N-diethylhydroxylamine.

This invention is particularly effective in reducing the color of aromatic diamines containing two primary amino groups and two to three alkyl groups attached to the benzene nucleus. Thus in one of its embodiments this invention provides a method of reducing the existing coloration of a liquid aromatic diamine having two primary amino groups and two to three alkyl substituents on a benzene ring, which method comprises blending into said a color-reducing amount of at least one N,N-dihydrocarbylhydroxylamine, most preferably N,N-diethylhydroxylamine.

Another embodiment involves reducing the existing coloration of an aromatic diamine containing two primary amino groups and two to three alkyl groups attached to the benzene nucleus, and inhibiting the re-development of color therein, which method comprises blending into the diamine a color-reducing amount of at least one N,N-dihydrocarbylhydroxylamine, and maintaining the resultant blend under an inert atmosphere.

Still another embodiment of this invention is a composition which comprises a liquid ring-polyalkyl-substituted aromatic diamine, with which has been blended a color-reducing amount of at least one N,N-dihydrocarbylhydroxylamine such that the color of said diamine has been reduced. Preferably this composition is maintained in a closed container (storage tank, tank car, tank truck, drum, can, bottle, etc.) having an internal head space containing an inert atmosphere, such as nitrogen.

A further embodiment provides an improvement in the production of diethyltoluenediamine wherein the diethyltoluenediamine is formed by a process comprising catalytic alkylation of toluenediamine with ethylene such that a clear liquid diethyltoluenediamine product having an amber-type coloration is formed. The improvement comprises blending with the diethyltoluenediamine product a color-reducing amount of at least one N,N-dihydrocarbylhydroxylamine such that the coloration of the liquid diethyltoluenediamine product is reduced, and maintaining the resultant blend under an inert atmosphere.

The above and other embodiments of this invention will become still further apparent from the ensuing description and appended claims.

Liquid Ring-Polyalkyl-Substituted Aromatic Diamines

Typically the amino groups of the diamines are both primary amino groups and these are in meta-positions or para-positions relative to each other. Preferred primary diamines of this type are those in which two of the alkyl groups are ethyl groups and the third is a methyl group, such as 3,5-diethyltoluene-2,4-diamine, 3,5-diethyltoluene-2,6-diamine, and mixtures thereof, especially mixtures which consist essentially of a major amount by weight (i.e., >50%) is 3,5-diethyltoluene-2,4-diamine and a minor amount (i.e., <50%) is 3,5-diethyltoluene-2,6-diamine, e.g., mixtures in which the ratio of these isomers is about 3.8 to about 4.5 parts by weight of 3,5-diethyltoluene-2,4-diamine per part by weight of 3,5-diethyltoluene-2,6-diamine.

Particularly preferred is an ar-polyalkylaromatic primary diamine product available in the marketplace as ETHACURE® 100 curative (Albemarle Corporation), the typical composition of which as specified by the manufacturer is:

3,5-diethyltoluene-2,4-diamine, 75.5–81.0%
3,5-diethyltoluene-2,6-diamine, 18.0–20.0%
Dialkylated m-phenylenediamines, 0.5–3.0%
Other trialkylated m-phenylenediamines, 0.0–0.4%
2,4,6-triethylbenzene-1,3-diamine, 0.0–0.1%

The sensitivity of ar-polyalkylaromatic primary diamines to color formation is illustrated by the fact that the manufacturer of this product specifies the typical appearance of ETHACURE® 100 curative as clear, amber liquid which darkens with time and exposure to air. Other characteristics of the product are that it does not contain m-phenylenediamine or methylenedianiline and does not have the staining characteristics of m-phenylenediamine. Because it is a low viscosity liquid the product is easy to mix with epoxy resins, and the resulting mixtures typically have a longer pot life than systems containing m-phenylenediamine or methylenedianiline. And the exotherm during the cure is low and allows the casting of large parts.

Methods for the preparation of ar-polyalkylaromatic primary diamines such as 3,5-diethyltoluene-2,4-diamine, and 3,5-diethyltoluene-2,6-diamine, are well known, and include catalyzed alkylation of toluenediamine with ethylene. Suitable catalysts which may be used include aluminum or aluminum chloride, an aluminum alkyl, an alkyl aluminum halide, or an aluminum anilide-type catalyst. See, for example, Stroh et al., *Angew. Chem.*, 1957, 69, 124, 127; GB 823,223; and Japan Kokai 05/201,934 A2 (1993). Other methods are described, for example, in EP 422,590 A2; EP 422,591 A2; and U.S. Pat. No. 4,760,185.

N,N-Dihydrocarbylhydroxylamine Color-Reducing Adjuvants

The N,N-dihydrocarbylhydroxylamine color reducing adjuvants utilized in the practice in this invention have the formula RRNOH where each R is, independently, a hydrocarbyl group such as an alkyl, alkenyl, cycloalkyl, cycloalkenyl, aryl, aralkyl, etc., which typically contains up to about 18 carbon atoms and preferably up to about 8 carbon atoms; or where the two R groups taken together constitute a single divalent hydrocarbyl group bonded to the nitrogen atom such that the nitrogen atom is part of a heterocyclic ring, which single divalent hydrocarbyl group typically contains up to about 20 carbon atoms and preferably up to about 10 carbon atoms including the carbon atoms of one or more hydrocarbyl substituents that may be, but need not be, present on the heterocyclic ring. Since the single divalent hydrocarbyl group has two different carbon atoms singly bonded to the nitrogen atom, such group is, in effect, two individual hydrocarbyl groups joined together to form a heterocyclic group containing the nitrogen atom as the hetero atom. Thus for the purposes of this disclosure and the appended claims the term "N,N-dihydrocarbylhydroxylamine" includes, is intended to include, and should be clearly understood to include, such single divalent hydrocarbyl groups. Particularly preferred color reducing adjuvants are the N,N-dialkylhydroxylamines in which each alkyl group, independently, contains in the range of 1 to about 6 carbon atoms, and N,N-diaralkylhydroxylamines in which each aralkyl group, independently, contains in the range of 7 to about 14 carbon atoms. A few illustrative examples of these particularly preferred color reducing adjuvants include N,N-dipropylhydroxylamine, N,N-diisopropylhydroxylamine, N,N-dibutylhydroxylamine, N,N-diisobutylhydroxylamine, N,N-dipentylhydroxylamine, N,N-dihexylhydroxylamine, N,N-di(4-methylpentyl)hydroxylamine, N,N-dibenzylhydroxylamine, N,N-di(4-methylbenzyl)hydroxylamine, and N,N-di(2-phenethyl)hydroxylamine. The most preferred color reducing adjuvant for use in the practice of this invention is N,N-diethylhydroxylamine.

Methods for the preparation of N,N-dihydrocarbylhydroxylamines are known and reported in the literature. For example, N,N-diethylhydroxylamine can be produced by oxidation of triethylamine with hydrogen peroxide or a percarboxylic acid to form triethylamine oxide, which decomposes upon strong heating to form N,N-diethylhydroxylamine and ethylene, or by oxidation of diethyl amine with hydrogen peroxide or a percarboxylic acid, to form N,N-diethylhydroxylamine. N,N-diethylhydroxylamine is used in photographic developers, as an oxygen scavenger in high pressure boiler water systems, and as a radical chain stopping reactant in polymerization reactions. It has also been described as an inhibitor of discoloration in monoalkylphenols and in aromatic amines. N,N-diethylhydroxylamine and N,N-dibenzylhydroxylamine are listed in the *Aldrich Catalog Handbook of Fine Chemicals*, 1996–1997, at pages 517 and 460, respectively, and thus are presently available from at least one commercial source.

Blending Operation

The compositions of this invention are readily formed by blending together one or more liquid ring-polyalkyl-substituted aromatic primary diamines and at least one N,N-dihydrocarbylhydroxylamine color-reducing adjuvant in suitable proportions. Typically, the color-reduction amounts of the N,N-dihydrocarbylhydroxylamine adjuvants of this invention fall somewhere in the range of about 100 to about 15,000 parts per million parts (wt/wt) of the ring-polyalkyl-substituted aromatic primary diamine. Preferred amounts fall in the range of about 500 to about 7500 parts of the adjuvant per million parts (wt/wt) of the ring-polyalkyl-substituted aromatic diamine. It will be understood and appreciated from this disclosure that in any given situation where a departure from the foregoing numerical ranges is deemed necessary or desirable, such departure can be undertaken, without departing from the purview and scope of this invention. The point here is that whatever the amount used, it must be sufficient to reduce the existing coloration of a color-possessing ring-polyalkyl-substituted aromatic primary diamine by a visually perceptible amount, provided the resultant reduced coloration is by visual perception less than the coloration produced by adding to another sample of the same color-possessing ring-polyalkyl-substituted aromatic primary diamine an equal amount of a clear, colorless inert organic diluent soluble in such diamine. This is what is meant herein (including the claims) by "a color reducing amount".

Other Components

Other suitable components may be included in the compositions of this invention. Among types of optional components from which suitable species may be selected are (i) one or more phenolic antioxidants such as 2,6-di-tert-butylphenol, 4-methyl-2,6-di-tert-butylphenol, 2,4-dimethyl-6-tert-butylphenol, etc., (ii) one or more inert liquid solvents or diluents, (iii) one or more isocyanate prepolymers, (iv) one or more polyether polyols, (v) one or more polyester polyols, (vi) one or more plasticizers, (vii) one or more pigments, or the like. Suitable combinations of two or more of (i) through (vii) may be included in the compositions, if desired. By "suitable" is meant that the component(s) must be compatible with the ar-polyalkylaromatic primary diamine and must not materially interfere with the color-reducing activity of the N,N-dihydrocarbylhydroxylamine color reducing adjuvant utilized pursuant to this invention.

Inert Atmospheres

As indicated above, it is preferred to place the ar-polyalkylaromatic primary diamine under an inert atmosphere promptly after the diamine has been treated with the N,N-dihydrocarbylydroxylamine color-reducing adjuvant pursuant to this invention. Indeed, the inert atmosphere can be applied during or even prior to the commencement of the color-reducing treatment. Once applied, the inert atmosphere should be maintained so as to minimize exposure of the treated diamine to air, and where necessary, replenishing the inert atmosphere after opening the container to the air such as when withdrawing a portion of the product for use. Suitable inert atmospheres include helium, neon, argon, krypton, and nitrogen, with nitrogen being preferred. The preferred way of maintaining the color-reduced ar-polyalkylaromatic primary diamine under an inert atmosphere is to place the color-reduced liquid ar-polyalkylaromatic primary diamine in a container such as a storage tank, a tank car, a tank truck, a drum, a can, a bottle or the like, in an amount that provides an interior headspace above the treated color-reduced diamine, fill the headspace with the inert atmosphere, and promptly seal the container to provide an air-tight closed container housing the color-reduced diamine product.

The following Examples illustrate the advantages achievable from the practice of this invention. In these Examples color reduction was determined using the standard Gardner Scale wherein the lower the numerical value, the lighter the color. These Examples are not intended to constitute limitations on the invention.

EXAMPLE 1

N,N-Diethylhydroxylamine was blended into a sample of diethyltoluenediamine (ETHACURE® 100 curative; Albemarle Corporation) to form a composition containing 200 parts by weight per million parts by weight of the diethyltoluenediamine curative (i.e., 200 ppm, wt/wt). The sample, which had an initial Gardner Color of 3, was stored at room temperature under nitrogen for 30 days. After the first day the Gardner color of the sample had dropped to 1 and remained at 1 throughout the remaining period of the test.

EXAMPLE 2

The procedure of Example 1 was repeated except that the concentration of the N,N-diethylhydroxylamine adjuvant in another sample of the same lot of the diethyltoluenediamine was 980 ppm (wt/wt). The Gardner Color again dropped from 3 to 1 in the first day and thereafter remained at 1 throughout the 30-day test period.

EXAMPLE 3

When the procedure of Example 1 was repeated using another sample of the same lot of the diethyltoluenediamine except that the N,N-diethylhydroxylamine adjuvant concentration was 4980 ppm (wt/wt), the Gardner Color again dropped from 3 to 1 within the first day and remained at 1 throughout the rest of the 30-day test period.

EXAMPLE 4

To a sample from another lot of diethyltoluenediamine having an initial Gardner color of 5 was added 1070 ppm of diethylhydroxyamine. After storing the treated sample under nitrogen overnight under nitrogen, the color had dropped to a Gardner rating of 1.

COMPARATIVE EXAMPLE

The test procedure of Example 1 was applied to a sample from the same lot of diethyltoluenediamine used in Example 1 and having an initial Gardner color of 3. In this case the sample was not treated with any N,N-diethylhydroxylamine adjuvant. The Gardner color remained at 3 for the first 10 days of the test, and then increased to 4 at which it remained for the remainder of the 30-day test period.

In other operations pursuant to this invention, it was found that when diethyltoluenediamine was treated with N,N-diethylhydroxylamine adjuvant at concentrations of 980 ppm (wt/wt) and 4980 ppm (wt/wt) and stored at 54° C. in containers at a volume of 1 to 1 with air, the Gardner color was again reduced from 3 to 1 within the first day and remained below 3 for two more days under these conditions before beginning to encounter progressive darkening. Under these same conditions diethyltoluenediamine treated with N,N-diethylhydroxylamine adjuvant at concentrations of 200 ppm (wt/wt) showed only a slight drop in coloration at the start and then underwent progressive darkening thereafter, thus indicating that 200 ppm is an insufficient concentration for the materials tested, unless the treated product is to be promptly stored under an inert atmosphere as in Example 1 above.

It is to be understood that the components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what preliminary chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent, published patent application, or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A method of reducing the existing coloration of a liquid ring-polyalkyl-substituted aromatic diamine, which method comprises blending into said ring-polyalkyl-substituted aromatic diamine a color-reducing amount of at least one dihydrocarbylhydroxylamine.

2. A method according to claim 1 wherein said ring-polyalkyl-substituted aromatic diamine consists essentially of at least one diethyltoluenediamine.

3. A method according to claim 1 wherein said ring-polyalkyl-substituted aromatic diamine consists essentially of at least one diethyltoluenediamine, and wherein said dihydrocarbylhydroxylamine consists essentially of diethylhydroxyl amine.

4. A method according to claim 1 wherein said ring-polyalkyl-substituted aromatic diamine consists essentially of a mixture of a major amount by weight of 3,5-diethyltoluene-2,4-diamine and a minor amount by weight of 3,5-diethyltoluene-2,6-diamine.

5. A method according to claim 4 wherein the dihydrocarbylhydroxylamine consists essentially of diethylhydroxylamine, and wherein the color-reducing amount is sufficient to reduce the Gardner Color rating of said aromatic diamine from a rating in the range of 3 to 5 to a rating of 1.

6. A method of reducing the existing coloration of a liquid ring-polyalkyl-substituted aromatic diamine, which method comprises blending into said ring-polyalkyl-substituted aromatic diamine a color-reducing amount of at least one dihydrocarbylhydroxylamine, and maintaining the resultant blend under an inert atmosphere.

7. A method according to claim 6 wherein said ring-polyalkyl-substituted aromatic diamine consists essentially of at least one diethyltoluenediamine.

8. A method according to claim 6 wherein said dihydrocarbylhydroxylamine consists essentially of diethylhydroxylamine.

9. A method according to claim 6 wherein said inert atmosphere consists essentially of nitrogen.

10. A method according to claim 6 wherein said ring-polyalkyl-substituted aromatic diamine consists essentially of at least one diethyltoluenediamine; wherein said dihydrocarbylhydroxylamine consists essentially of diethylhydroxylamine; and wherein said inert atmosphere consists essentially of nitrogen.

11. A method according to claim 6 wherein said ring-polyalkyl-substituted aromatic diamine consists essentially of a mixture of a major amount by weight of 3,5-diethyltoluene-2,4-diamine and a minor amount by weight of 3,5-diethyltoluene-2,6-diamine, and wherein said dihydrocarbylhydroxylamine consists essentially of diethylhydroxylamine.

12. A composition which comprises a liquid ring-polyalkyl-substituted aromatic primary diamine, with which has been blended a color-reducing amount of at least one dihydrocarbylhydroxylamine such that the color of said diamine has been reduced.

13. A composition according to claim 12 wherein the diamine consists essentially of at least one diethyltoluenediamine.

14. A composition according to claim 12 wherein the dihydrocarbylhydroxylamine consists essentially of diethylhydroxylamine.

15. A composition according to claim 12 wherein the diamine consists essentially of at least one diethyltoluenediamine, and wherein the dihydrocarbylhydroxylamine consists essentially of diethylhydroxylamine, and wherein said composition has a Gardner Color rating of 1 or 2.

16. A composition according to claim 12 wherein said composition is in a closed container having an internal head space containing an inert atmosphere.

17. A composition according to claim 15 wherein said composition is in a closed container having an internal head space containing an inert atmosphere.

18. In a process for the production of diethyltoluenediamine which comprises catalytically alkylating toluenediamine with ethylene such that a clear liquid diethyltoluenediamine product having an amber-type coloration is formed, the improvement which comprises blending with the diethyltoluenediamine product a color-reducing amount of at least one N,N-dihydrocarbylhydroxylamine such that the coloration of the liquid diethyltoluenediamine product is reduced, and maintaining the resultant blend under an inert atmosphere.

19. The improvement according to claim 18 wherein the dihydrocarbylhydroxylamine consists essentially of diethylhydroxylamine, and wherein the coloration of said product is reduced to a Gardner Color rating of 1 or 2.

* * * * *